(12) United States Patent
Fattal et al.

(10) Patent No.: US 7,876,444 B2
(45) Date of Patent: Jan. 25, 2011

(54) PLASMONIC CONVEYOR APPARATUS, SYSTEM AND METHOD

(75) Inventors: David Fattal, Mountain View, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 335 days.

(21) Appl. No.: 12/262,151

(22) Filed: Oct. 30, 2008

(65) Prior Publication Data

US 2010/0020327 A1    Jan. 28, 2010

Related U.S. Application Data

(60) Provisional application No. 61/083,543, filed on Jul. 25, 2008.

(51) Int. Cl.
*G01N 21/55* (2006.01)
(52) U.S. Cl. .................... 356/445; 356/301
(58) Field of Classification Search ............ 356/244, 356/246, 326, 432, 441, 445–448; 385/12.17, 385/30; 372/26, 28, 32, 45.01–46.016, 38.01–38.02, 372/96; 422/82.05, 52.11
See application file for complete search history.

(56) References Cited

U.S. PATENT DOCUMENTS

| | | |
|---|---|---|
| 6,897,950 B2 | 5/2005 | Li et al. |
| 7,151,598 B2 | 12/2006 | Poponin |
| 7,238,477 B2 | 7/2007 | Su et al. |
| 2004/0191778 A1 | 9/2004 | Inaoka |
| 2006/0119853 A1* | 6/2006 | Baumberg et al. .......... 356/445 |
| 2008/0154431 A1 | 6/2008 | Defries et al. |
| 2009/0020426 A1* | 1/2009 | Thundat et al. ............. 204/450 |

OTHER PUBLICATIONS

Fredrik Svedberg et al., "Creating Hot Nanoparticle Pairs for Surface-Enhanced Raman Spectroscopy through Optical Manipulation," Nano Lett., vol, 6, No. 12, 2006, pp. 2639-2641.

K.-H. Su et al., "Interparticle Coupling Effects on Plasmon Resonances of Nanogold Particles," Nano Lett., vol. 3, No. 8, 2003, pp. 1087-1090.

Troy A. Alexander et al.,"Near-Infrared Surface-Enhanced-Raman-Scattering-Mediated Detection of Single Optically Trapped Bacterial Spores," Applied Spectroscopy, vol. 57, No. 11, 2003, pp. 1340-1354.

(Continued)

*Primary Examiner*—Tarifur Chowdhury
*Assistant Examiner*—Michael LaPage

(57) ABSTRACT

A plasmonic conveyor, system and method of plasmonic conveyance employ a surface plasmon that is controllably moved on a surface of a plasmonic element. The conveyor includes a first plasmonic element and a second plasmonic element that individually supports a respective surface plasmon. The conveyor further includes a controller that provides controlled movement of a location of the respective surface plasmon on a surface of the plasmonic element. The controlled movement facilitates translocation of an analyte particle around a periphery of the respective plasmonic element using a high field region of the respective surface plasmon. The system includes the conveyor and an excitation signal source that provides an excitation signal having one or both of a polarization and a frequency that are controllably variable. The method includes exciting a surface plasmon with the excitation signal and moving a location of the excited surface plasmon.

15 Claims, 7 Drawing Sheets

OTHER PUBLICATIONS

Kerstin Ramser et al., "Resonance Raman spectroscopy of optically trapped functional erythrocytes," Journal of Biomedical Optics, May/Jun. 2004, vol. 9, No. 3, pp. 593-600.

Christy L. Haynes et al., "Surface Enhanced Raman Spectroscopy," Analytical Chemistry, Sep. 1, 2005, pp. 338A-346A.

Pamela Jordan et al., "Surface—enhanced resonance Raman scattering in optical tweezers using co-axial second harmonic generation," Optics Express, vol. 13, No. 11, May 30, 2005, pp. 4148-4153.

Hongxing Xu et al., "Surface-Plasmon-Enhanced Optical Forces in Silver Nanoaggregates," Physical Review Letters, vol. 89, No. 24, Dec. 9, 2002, pp. 246802-1 to 246802-4.

Andrea Tao et al., "Tunable plasmonic lattices of silver nanocrystals," Nature Nanotechnology, vol. 2, Jul. 2007, www.nature.com/naturenanotechnology, pp. 435-440.

* cited by examiner

PLASMONIC CONVEYOR APPARATUS, SYSTEM AND METHOD

CROSS-REFERENCE TO RELATED APPLICATIONS

The present application claims priority from provisional application Ser. No. 61/083,543, filed Jul. 25, 2008, the contents of which are incorporated herein by reference in their entirety.

STATEMENT REGARDING FEDERALLY SPONSORED RESEARCH OR DEVELOPMENT

N/A

BACKGROUND

1. Technical Field

The invention relates to analyte particle manipulation. In particular, the invention relates to using surface plasmons to manipulate analyte particles.

2. Description of Related Art

The manipulation and analysis of extremely small analyte particles has attracted a great deal of attention in recent years. For example, spectral emission-based analysis methodologies such as, but not limited to, surface enhanced Raman spectroscopy (SERS) have been shown to have promise for analyzing single cells, bacterial spores, certain individual molecules, and similar nano-scale analyte particles.

However, the principal difficulty in performing such nano-scale analysis is often in collocating a target analyte particle and an analysis region so that analysis may occur. For example, SERS generally relies on collocation of the analyte molecules or particles and a region of high field intensity (i.e., a hot spot) on a SERS active substrate often referred to as a 'hot spot'. Typically, collocation of an analyte particle with a SERS hot spot is an essentially random event. As such, in many cases the Raman active substrate is typically exposed to a large volume of media containing analyte particles in the hope that some analyte particles find their way to the SERS hot spot so that an enhanced Raman spectral response signal is generated. Unfortunately, a size of a hot spot on the Raman active substrate is generally extremely small which tends to adversely affect the probability of capture and subsequent analysis. A similar issue of analyte particle and active region exists in many other analytical techniques.

Attempts to address the collocation problem and further, in the interest of simply being able to work with nano-scale analyte particles on an individual basis, various nano-manipulation techniques have been developed. For example, optical tweezer that employ an optical field gradient to trap and hold analyte particles have been demonstrated. The optical tweezer enables an analyte particle to be selected, captured and held by an optical field of the tweezer. Once held by the optical tweezer, the analyte particle may be delivered to a SERS hot spot, for example, by essentially moving the optical field of the optical tweezer (often by a mechanical means) to a location of the hot spot. However, providing precise movement of the optical field and knowing where to place a captured analyte particle (e.g., where the hot spot is located) often represent significant obstacles to the use of optical tweezers.

As such, means for capturing and controllably manipulating analyte particles is of great interest both to the field of analysis and in a general area of nano-manipulation. Providing such means would satisfy a long felt need.

BRIEF SUMMARY

In some embodiments of the present invention, a plasmonic conveyor is provided. The plasmonic conveyor comprises a first plasmonic element that supports a first surface plasmon. The plasmonic conveyor further comprises a second plasmonic element that supports a second surface plasmon. The second plasmonic element is adjacent to the first plasmonic element. The plasmonic conveyor further comprises means for controlling a location of the first surface plasmon. The means for controlling provides controlled movement of the location on a surface of the first plasmonic element. The controlled movement of the location of the first surface plasmon facilitates translocation of an analyte particle along a periphery of the First plasmonic element. The analyte particle is carried by a high field region of the first surface plasmon.

In other embodiments of the present invention, a plasmonic conveyance system is provided. The plasmonic conveyance system comprises a plurality of plasmonic elements that each individually supports a surface plasmon. A first plasmonic element of the plurality is adjacent to a second plasmonic element of the plurality. The plasmonic conveyance system further comprises an excitation signal source that provides an excitation signal having a controllably variable one or both of polarization and frequency. The excitation signal excites a respective surface plasmon. The controllably variable one or both of polarization and frequency controls and moves a location of the excited surface plasmon to transport an analyte particle. The analyte particle is carried by a high field region of the excited surface plasmon.

In other embodiments of the present invention, a method of plasmonic conveyance is presented. The method of plasmonic conveyance comprises exciting a surface plasmon on a first plasmonic element of a plurality or plasmonic elements using am excitation field having one or both of a polarization and a frequency that is controllably variable. The method of plasmonic conveyance further comprises varying one or both of the polarization and the frequency of the excitation field to move a location of the excited surface plasmon, wherein the surface plasmon is moved on a surface of the first plasmonic element. An analyte particle trapped in a high field region of the excited surface plasmon is transported around a periphery of the first plasmonic element by the moved location of the excited surface plasmon.

Certain embodiments of the present invention have other features that are one of in addition to and in lieu of the features described hereinabove. These and other features of the invention are detailed below with reference to the following drawings.

BRIEF DESCRIPTION OF THE DRAWINGS

The various features of embodiments of the present invention may be more readily understood with reference to the following detailed description taken in conjunction with the accompanying drawings, where like reference numerals designate like structural elements, and in which.

DETAILED DESCRIPTION

Figure 1A:
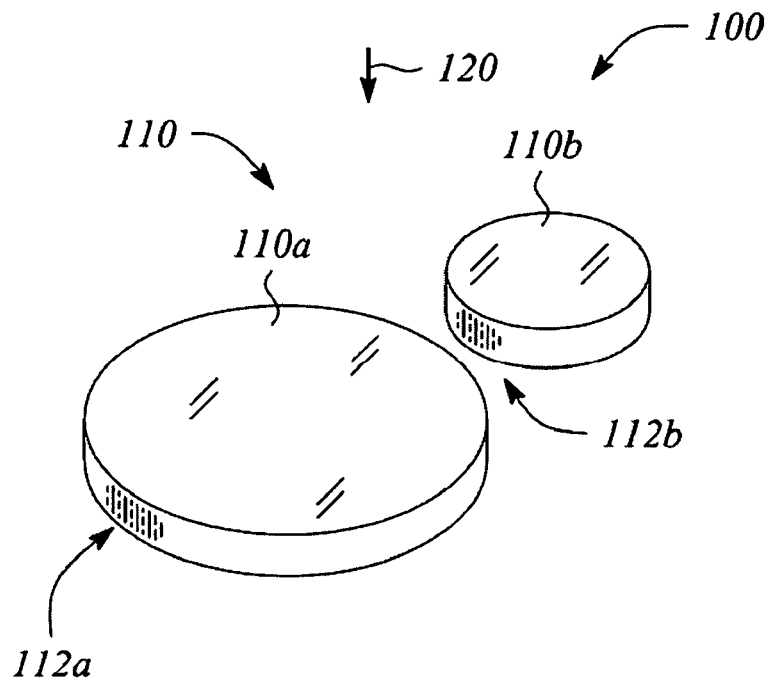
FIG. 1A illustrates a perspective view of a plasmonic conveyor, according to an embodiment of the present invention.

Embodiments of the present invention facilitate manipulation and analysis of an analyte particle using a surface plasmon. In particular, a high field region associated with a surface plasmon is employed to trap and transport the analyte particle. The surface plasmon is controllably moved on a plasmon supporting surface. The analyte particle trapped by the high field region is transported along the plasmon supporting surface by the controllably moved surface plasmon. In some embodiments, the transported analyte particle is further transferred from the high field region to a high field region of another surface plasmon. As such, embodiments of the present invention essentially act as a plasmonic conveyor. In some embodiments, the plasmonic conveyor of the present invention moves one or more analyte particles from one point to another.

In particular, some embodiments the plasmonic conveyor 'traps' an analyte particle and moves the trapped analyte particle to a location that facilitates analysis of the analyte particle. For example, the trapped analyte particle may be moved from a source of analyte particles to a region of a local 'hot spot' on a Raman active surface for subsequent analysis using surface enhanced Raman spectroscopy (SERS). In another example, the plasmonic conveyor essentially functions as a transport switch that selectively transports the analyte particle from an input to a selected one of a plurality of outputs.

Embodiments of the present invention employ a surface plasmon that is excited on a surface of a plasmonic element. The surface plasmon is excited by exposing the plasmonic element to an excitation signal. An electromagnetic field of the excitation signal interacts with electrons in the plasmonic element surface to excite the surface plasmon. For example, a laser may be used to illuminate the plasmonic element with an optical excitation signal.

In general, a particular choice of a frequency or a frequency range of the excitation signal may depend on one or more of a dielectric environment, a characteristic of the plasmon supporting material (e.g., a metal type), and a size/shape of the plasmonic element. For example, the laser may produce an optical signal in a frequency range between ultra violet (UV) frequencies and near infrared (NIR) frequencies may be used to excite a surface plasmon on a plasmonic element comprising a plasmon supporting material such as, but not limited to, a noble metal. In another example, the optical signal may have a wavelength between about 400 nanometers (nm) and 800 nm.

Various embodiments of the present invention employ a surface plasmon that is moved by means for controlling a location of the surface plasmon. In some embodiments, the means for controlling a location comprises a changeable characteristic of the excitation signal. In particular, a location of the excited surface plasmon may be controlled by one or both of a frequency of the excitation signal and a polarization of the excitation signal. By changing one or both of frequency and polarization, the location of the surface plasmon may be controllably moved along the surface of the plasmonic element.

In some embodiments, the plasmonic element may be illuminated by an exemplary linearly polarized excitation signal having a controllable polarization (e.g., using a laser with a controllable polarizer). The excitation signal may be incident on a top of the plasmonic element, for example. An initial location of the surface plasmon is established by an initial polarization of the excitation signal (e.g., a vertical linear polarization). Once excited, the surface plasmon may be controllably moved along or around a periphery of the plasmonic element by changing or rotating the polarization of the excitation signal.

For example, the polarization of the excitation signal may be rotated 180 degrees in an essentially continuous manner (e.g., from the initial vertical polarization to a horizontal polarization). The surface plasmon excited by the excitation field essentially follows the rotating polarization such that the surface plasmon moves from a first location established by the initial polarization to second location on an opposite side of the plasmonic element. Essentially, rotating the polarization by 180 degrees provides movement of the surface plasmon along the surface of the plasmonic element from one side to another thereof Continuing the polarization rotation (i.e., going beyond 180 degrees) will eventually result in the surface plasmon circumscribing the periphery of the plasmonic element and returning to the first location.

In some embodiments, the plasmonic element may be illuminated by an exemplary excitation signal having a controllably variable frequency (e.g., by using a frequency tunable laser). A location of the surface plasmon may be changed and/or switched on and off by changing the frequency of the excitation signal, for example.

Advantageously, a high field region of or associated with the surface plasmon moves along with the moving surface plasmon. The field of the high field region comprises an electric field, in some embodiments. Thus, when the surface plasmon is moved around the plasmonic element circumference, the high field region similarly moves around the plasmonic element. Moreover, any analyte particles that may be trapped in the high field region also move around the plasmonic element. As a result, the exemplary one or both of rotating polarization and controllably varying frequency may be used to transport analyte particles around the periphery of the plasmonic element. Furthermore, the translocation is entirely under the control of the controllable one or both of polarization and frequency of the excitation signal.

As used herein, the term 'plasmonic element' is defined as a three dimensional body having a surface that supports the surface plasmon. In particular, the plasmonic element comprises a plasmon supporting material, which in some embodiments, may be throughout the plasmonic element. In other embodiments, the plasmon supporting material may be a coating or layer on an exterior surface of the plasmonic element. For example, the plasmonic element may have a surface that comprises a noble metal. In another example, the plasmonic element may be essentially a solid metal or organometallic structure.

The plasmonic element may have any of a wide variety of shapes including, but not limited to, a disk, a sphere or more generally an oblate spheroid, and a dome or hemisphere. In some embodiments, the plasmonic element has an essentially smooth surface. In other embodiments, the plasmonic element may have protrusions or similar surface regions that exhibit a localized high radius of curvature. For example, the plasmonic element may have a cross section that resembles a tear drop. Moreover, embodiments of the plasmonic element of the present invention have generally small strictures. For example, the plasmonic element may be between about 1 micron (μm) and about 10 nanometers (nm) in overall extent, according to some embodiments.

A 'surface plasmon' is defined herein as a surface wave or plasma oscillation of a free electron gas at a surface of a plasmon supporting material. The surface plasmon also may be considered as a quasiparticle representing a quantization of a plasma oscillation in a manner analogous to the representation of an electromagnetic oscillation quantization as a photon. For example, collective oscillations of a free electron gas in a surface of a noble metal induced by an incident electromagnetic wave at optical frequencies may be represented in terms of surface plasmons. Furthermore, characteristics of an interaction between the surface plasmons and the surface may be characterized in terms of plasmonic modes. In particular, plasmonic modes represent characteristics of surface plasmons in much the same way that electromagnetic oscillations are represented in terms of electromagnetic or optical modes.

Surface plasmons and by extension, plasmonic modes, are confined to a surface of a material that supports surface plasmons. For example, an optical signal incident from a vacuum or a dielectric material on a surface of a surface plasmon supporting material may excite a surface plasmon. In some cases, the surface plasmon is essentially stationary (e.g., a standing wave) and in other cases, the surface plasmon may propagate along the surface. Surface plasmon supporting materials are materials such as, but not limited to, certain organometallics that exhibit a dielectric constant having a negative value real part and metals. Noble metals such as, but not limited to, gold (Au), silver (Ag) and copper (Cu) are materials that are known to support surface plasmons at or near optical frequencies.

A surface plasmon on a surface of a plasmon supporting material creates a local high field region adjacent to and above (i.e., just outside of) the plasmon supporting material. Specifically, the surface plasmon generates an evanescent field in the region above the surface plasmon. The generated evanescent field typically exhibits a field intensity that is higher than and, in some embodiments is much higher than, an average field intensity in a general vicinity of the plasmon supporting material. For example, the field intensity of the evanescent field above the surface plasmon is generally much higher than a field intensity of an electromagnetic field (e.g., optical field) used to excite the surface plasmon. As such, the region above or adjacent to the surface plasmon containing the generated evanescent field is referred to herein as the 'high field region'.

The high field region has a size or extent that is proportional to a size of the plasmonic element. On the other hand, an intensity of the high field region is inversely proportional to the size of the plasmonic element. As such, a larger plasmonic element will have a correspondingly larger high field region than a high field region of a smaller plasmonic element when illuminated by the same excitation signal. However, the intensity of the high field region of the smaller plasmonic element will be greater than that of the high field region of the larger plasmonic element. As such, a larger plasmonic element may be used to attract and trap analyte particles from a diffuse stream or source, due to the relatively larger high field region, for example. The smaller plasmonic element with its relatively higher field intensity may serve as a relatively better location for providing analysis results that are based on a local field intensity (e.g., SERS), for example.

For simplicity herein, no distinction is made between various materials that may be employed to support a surface plasmon unless such distinction is necessary for proper understanding. Instead, all materials that are known to support or potentially may support a surface plasmon are generically referred to as 'plasmon supporting materials'. Further, as used herein, the article 'a' is intended to have its ordinary meaning in the patent arts, namely 'one or more'. For example, 'a plasmonic element' generally means 'one or more plasmonic elements' and as such, 'the plasmonic element' means 'the plasmonic element(s)' herein. Also, any reference herein to 'top', 'bottom', 'upper', 'lower', 'up', 'down', 'left' or 'right' is not intended to be a limitation herein. Moreover, examples herein are intended to be illustrative only and are presented for discussion purposes and not by way of limitation.

Figure 1B:
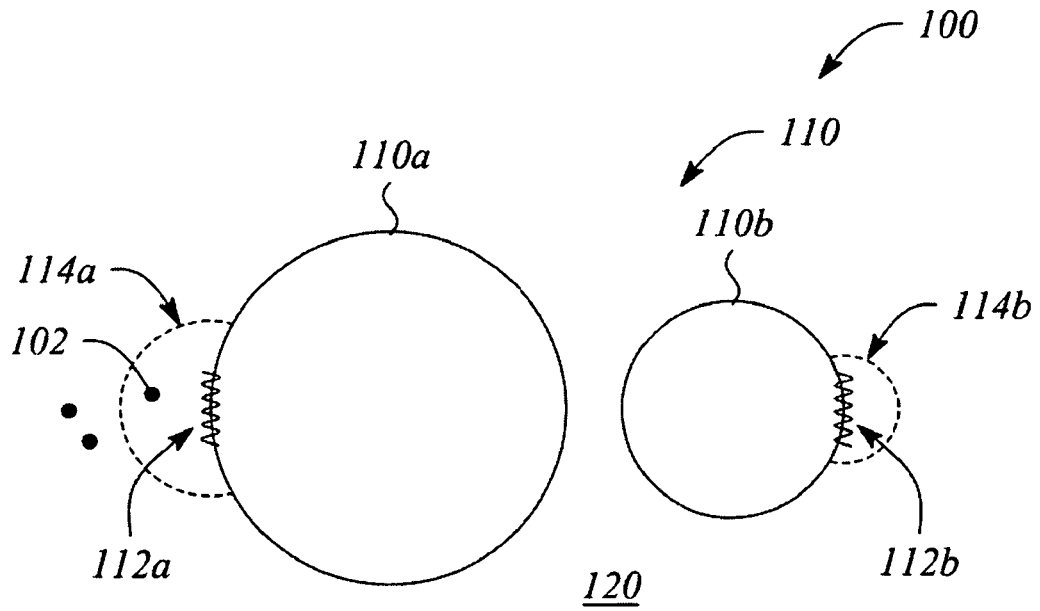
FIG. 1B illustrates a top view of the plasmonic conveyor illustrated in FIG. 1A, according to an embodiment of the present invention.

FIG. 1A illustrates a perspective view of a plasmonic conveyor 100, according to an embodiment of the present invention. FIG. 1B illustrates a top view of the plasmonic conveyor 100 illustrated in FIG. 1A, according to an embodiment of the present invention. The plasmonic conveyor 100 provides controlled movement of a location of a surface plasmon. The controlled movement of the location of the surface plasmon, in turn, facilitates translocation of an analyte particle 102 (illustrated in FIG. 1B by way of example). Specifically, the analyte particle 102 is carried by a high field region of the surface plasmon and thus, moves along with the surface plasmon.

In particular as illustrated in FIGS. 1A and 1B, the plasmonic conveyor 100 comprises a plurality of plasmonic elements 110. Each plasmonic element 110 of the plurality comprises a plasmon supporting material. In some embodiments (not illustrated), the plurality of plasmonic elements 110 may be supported by a substrate. The exemplary plasmonic elements 110 illustrated in FIGS. 1A and 1B are depicted as metallic disks arranged essentially coplanar to one another.

A first plasmonic element 110a of the plurality of plasmonic elements 110 supports a first surface plasmon 112a. A second plasmonic element 110b of the plurality of plasmonic elements 110 supports a second surface plasmon 112b. The second plasmonic element 110b is adjacent to but spaced apart from the first plasmonic element 110a. In particular, a circumferential edge of the second plasmonic element 110b is located next to, but spaced apart from, the circumferential edge of the first plasmonic element 110a. Each of the first surface plasmon 112a and second surface plasmon 112b has a respective high field region 114a, 114b.

The plasmonic conveyor 100 further comprises means for controlling a location of the first surface plasmon 112a. The means for controlling a location of the first surface plasmon 112a provides controlled movement of the location on a surface of the first plasmonic element 110a. In some embodiments, the means for controlling comprises a controllably variable polarization of a field or signal incident (i.e., 'incident field') on the plurality of plasmonic elements 110. In another embodiment, the means for controlling comprises a controllably variable or switchable frequency of the incident field. In yet other embodiments, the means for controlling comprises both the controllably variable polarization and the controllably variable frequency of the incident field.

The illustrated plasmonic conveyor 100 further comprises an excitation signal 120 (e.g., an optical signal). The excitation signal is incident on one or both of the first plasmonic element 110a and the second plasmonic element 110b. The incident excitation signal 120 excites one or both of the first surface plasmon 110a and the second surface plasmon 110b. In some of these embodiments, the means for controlling the location comprises one or both of a controllably variable polarization and controllably variable frequency of the excitation signal 120.

In particular, the excitation signal 120 may comprise a polarization that is controllably variable from a first polarization to a second polarization. For example, the polarization of the excitation signal 120 may have a linear polarization that is controllably variable (i.e., may be rotated) from a horizontal polarization (e.g., 0 degrees) to a second horizontal polarization (e.g., 180 degrees) passing through a vertical polarization (e.g., 90 degrees). In other example, the polarization may an elliptical polarization having a major axis that is continuously variable from essentially 0 degrees to about 360 degrees.

In another embodiment, the excitation signal 120 may comprise a frequency that is controllably variable from a first frequency to a second frequency. For example, the excitation signal 120 may have a wavelength that may be varied or switched across a range from about 400 nm to about 800 nm.

In some embodiments, the means for controlling further controls a location of the second surface plasmon 112b on the second plasmonic element 110b. In other embodiments (not illustrated), the plasmonic conveyor 100 further comprises means for separately controlling a location of the second surface plasmon 112b. In yet other embodiments, the location of the second surface plasmon 112b is either essentially not controlled or at least not movably controlled.

FIGS. 2A-2E illustrate a sequence of top views of a plasmonic conveyor 100, according to an embodiment of the present invention. In particular, FIGS. 2A-2E illustrate the plasmonic conveyor 100 as the surface plasmon 112a of the first plasmonic element 110a is controllably moved by a variable polarization of the excitation signal 120. Also illustrated in FIGS. 2A-2E is both a translocation of an analyte particle 102 around the circumferential edge of the first plasmonic element 110a from an analyte particle source 104 and a transfer of the analyte particle 102 to a high field region 114b of the second surface plasmon 112b of the second plasmonic element 110b.

Figure 2A:
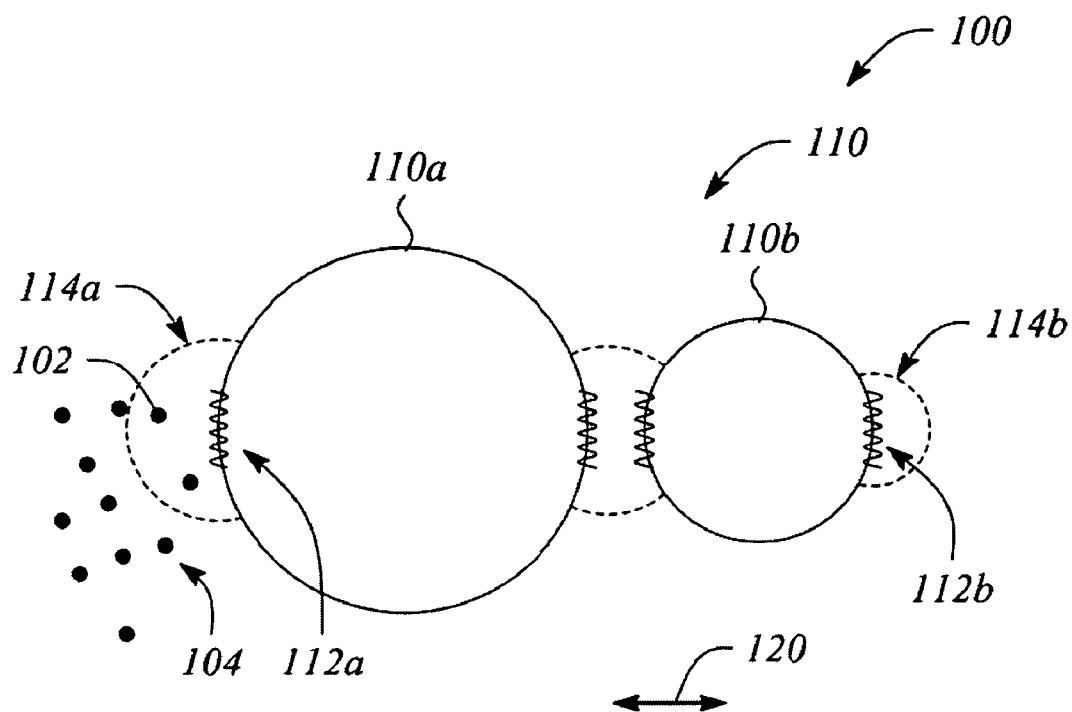
FIGS. 2A-2E illustrate a sequence of top views of a plasmonic conveyor, according to an embodiment of the present invention.

In FIG. 2A, the plasmonic conveyor 100 is illustrated as illuminated by an excitation signal 120 (e.g. a plane wave) having a controllably variable linear polarization, by way of example. In FIGS. 2A-2E, the variable linear polarization is depicted as a double-headed arrow associated with excitation signal 120. The excitation signal 120 excites the first surface plasmon 112a on the first plasmonic element 110a. As illustrated in FIG. 2A, the linear polarization is depicted as horizontally oriented (i.e., 0 degrees) which establishes a location of the first surface plasmon 112a adjacent to a source 104 (e.g., a stream) of analyte particles 102. One or more of the analyte particles 102 is attracted to and subsequently trapped by the high field region 114a of the first surface plasmon 112a. The excitation signal 120 also excites and establishes a location of the second surface plasmon 112b with an associated high field region 114b on the second plasmonic element 110b, as illustrated.

Furthermore as illustrated, the linearly polarized excitation signal 120 actually produces a pair of surface plasmons on opposite sides of each of the disk-shaped plasmonic elements 110a, 110b. Only the surface plasmons 112a, 112b of the respective pairs are labeled for simplicity of illustration. In general, a specific configuration and distribution of surface plasmons produced by an excitation signal 120 is a function of the polarization (e.g., linear, elliptical, etc.) of the excitation signal 120, the frequency of the excitation signal 120, and a shape of the plasmonic elements 110a, 110b, according to plasmonic modes associated the plasmonic elements 110a, 110b.

Figure 2B:
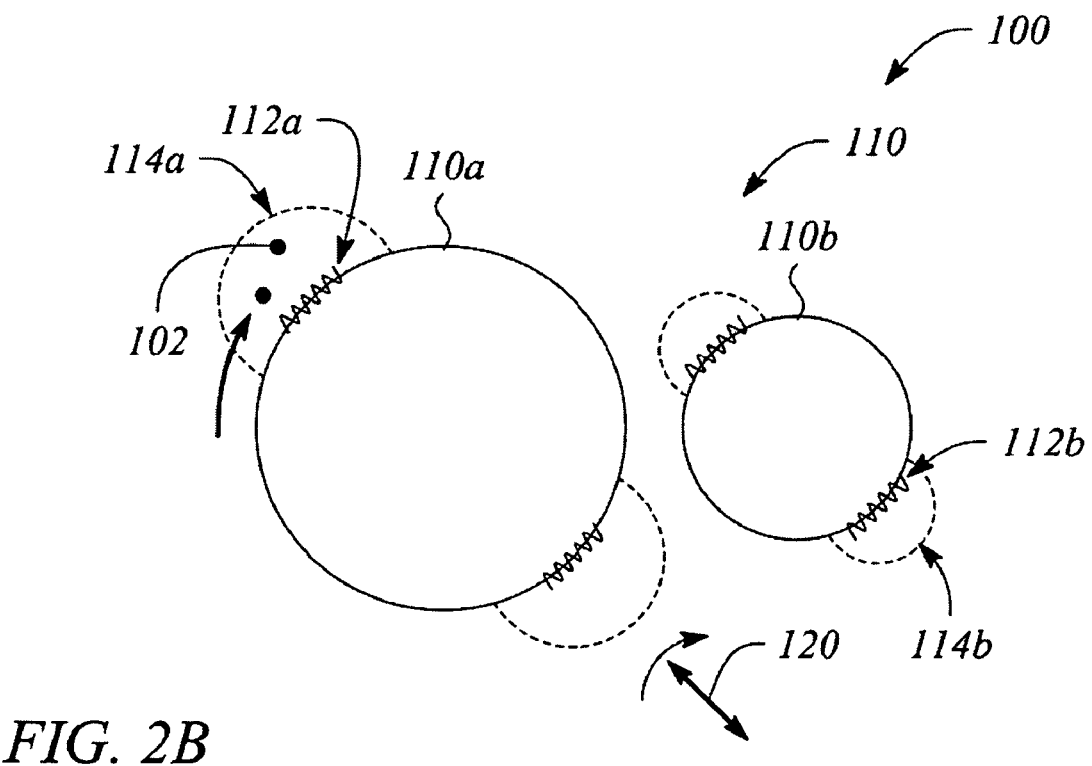

FIG. 2B illustrates the plasmonic conveyor 100 after the linear polarization of the excitation signal 120 has been rotated about 45 degrees towards a vertical polarization. Rotating the linear polarization has moved a location of the first surface plasmon 112a about 45 degrees around the periphery of the disk-shaped first plasmonic element 110a, as illustrated. Movement of the first surface plasmon 112a has similarly moved the trapped analyte particles 102 within the high field region 114a. As illustrated, the second plasmon 112b is also similarly moving around a periphery of the second plasmonic element 110b.

Figure 2C:
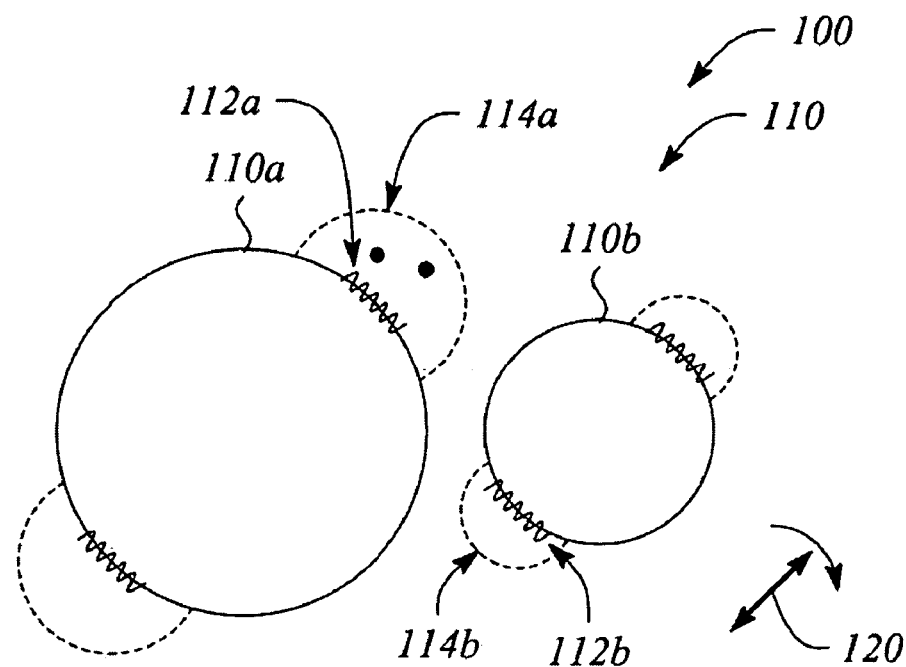

FIG. 2C illustrates the plasmonic conveyor 100 following further rotation of the linear polarization through and past a vertical polarization. Specifically, the linear polarization of the excitation signal 120 has been rotated about 135 degrees from horizontal, as illustrated in FIG. 2C. Concomitant with the polarization rotation, the location of the surface plasmon 112a and surface plasmon 112b and their associated high field regions 114a, 114b have also rotated about 135 degrees.

Figure 2D:
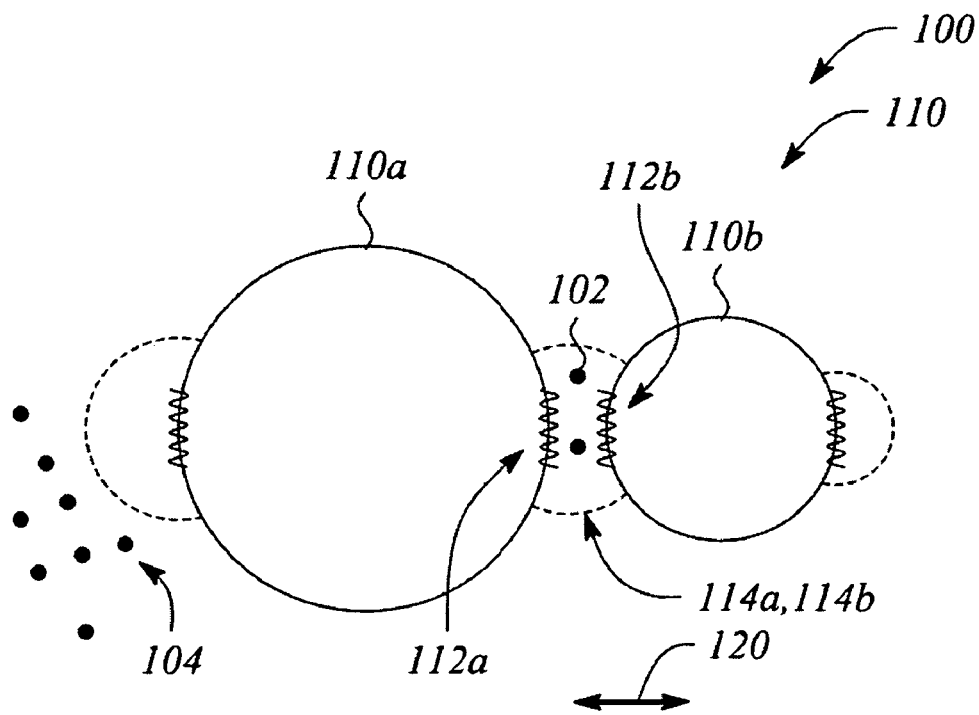

FIG. 2D illustrates the plasmonic conveyor 100 as the polarization rotation reaches another horizontal polarization (e.g., a rotation of 180 degrees). The first surface plasmon 112a is oriented on a side of the plasmonic element 110a adjacent to the second plasmonic element 110b. The analyte particles 102 have been transported by the movement of the first surface plasmon 112a from a side of the first plasmonic element 110a adjacent to the source 104 to a side adjacent to the second plasmonic element 110b.

Moreover, as illustrated in FIG. 2D, the analyte particles 102 have been moved to and are within a combined high field region comprising the high field regions 114a, 114b of both of the first surface plasmon 112a and the second surface plasmon 112b. As such, the trapped and transported (i.e., translocated) analyte particles 102 are subjected to a local field that is a sum of the fields of the two high field regions 114a, 114b. Advantageously, the field intensity of the combined high field regions 114a, 114b may significantly increase a SERS output from the analyte particles 102 compared to an output when the analyte particles 102 are not subjected to the combined high field regions, for example.

Figure 2E:
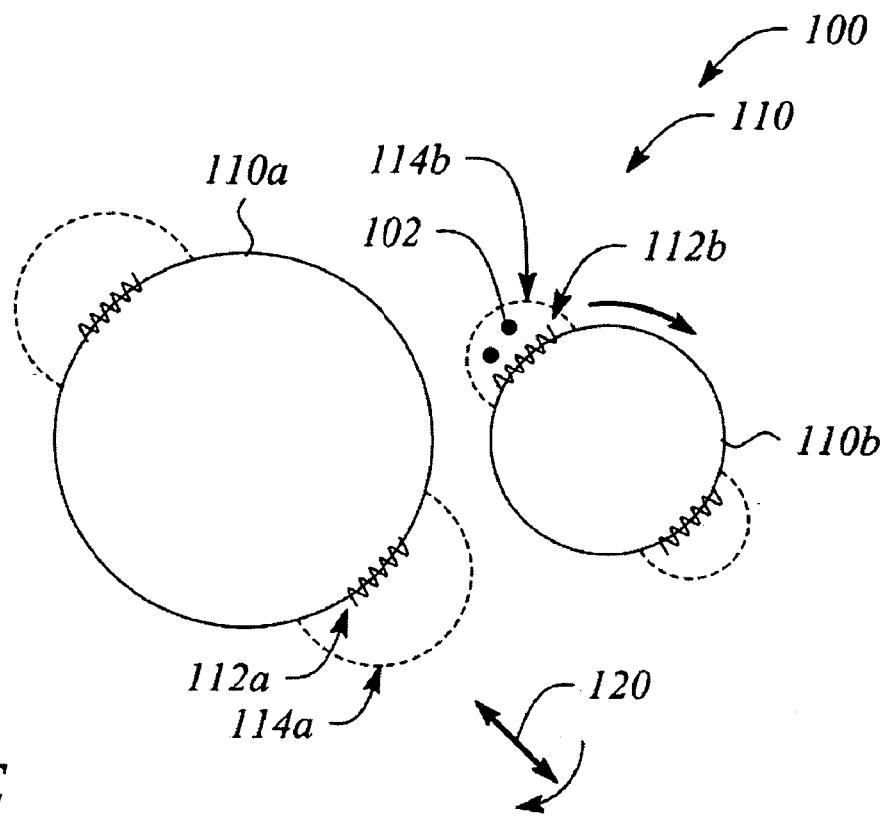

FIG. 2E illustrates the plasmonic conveyor 100 after the polarization has been further rotated beyond the horizontal polarization (e.g., rotated to about 225 degrees). The analyte particles 102 have been transferred from the high field region 114a of the first surface plasmon 112a to the high field region 114b of the second surface plasmon 112b. As such, the analyte particles 102 are illustrated as moving with the second surface plasmon 112b around the periphery of the second plasmonic element 110b.

In some embodiments, a transfer of analyte particles 102 such as that illustrated in FIG. 2E is facilitated by a difference in a field intensity between two high field regions (e.g., 114a, 114b) of two adjacent surface plasmons (e.g., 112a, 112b as illustrated in FIG. 2D). A high field region having a higher field intensity will preferentially attract and trap an analyte particle that is in and moving with a high field region having a lower field intensity. Moreover, a field intensity of a high field region associated with a surface plasmon in a surface of a plasmonic element decreases as the size of a plasmonic element increases. Thus, transfer of the analyte particles 102 from the high field region 114a of the first surface plasmon 112a to the high field region 114b of the second surface plasmon 112b may be facilitated by the second plasmonic element 110b being smaller than the first plasmonic element 110a. Furthermore, analyte particles may be transferred to a third plasmonic element (not illustrated) of the plurality of plasmonic elements 110 when the third plasmonic element is smaller than the second plasmonic element Such transfer between adjacent, sequentially smaller plasmonic elements (e.g., 110a, 110b, etc.) simultaneously illuminated by the excitation signal 120 is essentially a passive process depending only on a size difference of the various plasmonic elements in a cascade.

In some embodiments, other means for controlling transfer of analyte particles other than or in addition to the size of the plasmonic element and the concomitant differential field intensity may be employed. For example, separate excitation signals may be directed at adjacent plasmonic elements. Transfer may be provided by switching on the excitation signal directed at a second adjacent plasmonic element while the excitation signal directed at a first adjacent plasmonic element is switched off, for example.

In another example, changing a frequency of the excitation signal (i.e., the controllably variable frequency) from a plasmonic resonant frequency of a first plasmonic element to a plasmonic resonant frequency of a second adjacent plasmonic element may be used to accomplish transfer. The frequency change in conjunction with the different plasmonic resonant frequencies of the respective plasmonic elements essentially switches off the surface plasmon on the first plasmonic element while simultaneously switching on the surface plasmon on the second adjacent plasmonic element. Switching off and on the respective surface plasmons provides the transfer of the analyte particle in the example. The plasmonic resonant frequency of the plasmonic elements may be a function of one or more of size, shape, and surface material of a respective plasmonic element, for example.

In yet another example, the plasmonic resonant frequency in conjunction with the controllably variable frequency of the excitation signal also may be used to move a location of the surface plasmon according to plasmonic modes associated with the plasmonic resonant frequency of the various plasmonic elements, in some embodiments. For example, by changing the frequency of the excitation signal, nodes of plasmonic resonance modes of the plasmonic elements may be moved around the plasmonic elements. Moving the nodes using the controllably variable frequency essentially provides movement of the trapped analyte particles along the surface of the plasmonic elements.

Figure 3A:
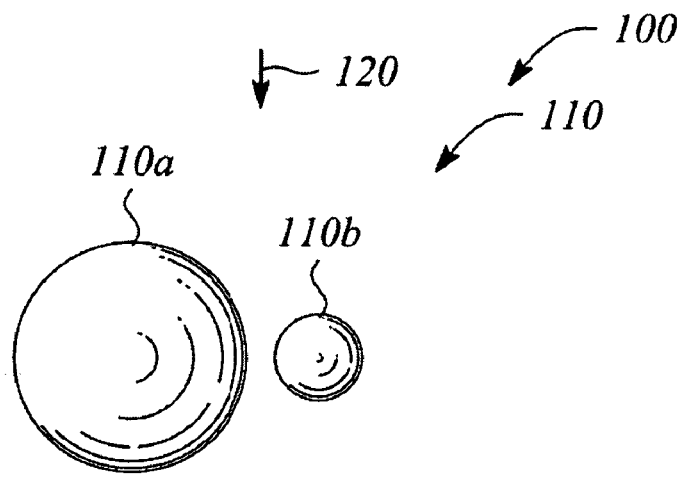
FIGS. 3A-3B illustrate a top view and a perspective view of a conveyor, according to another embodiment of the present invention.
Figure 3B:
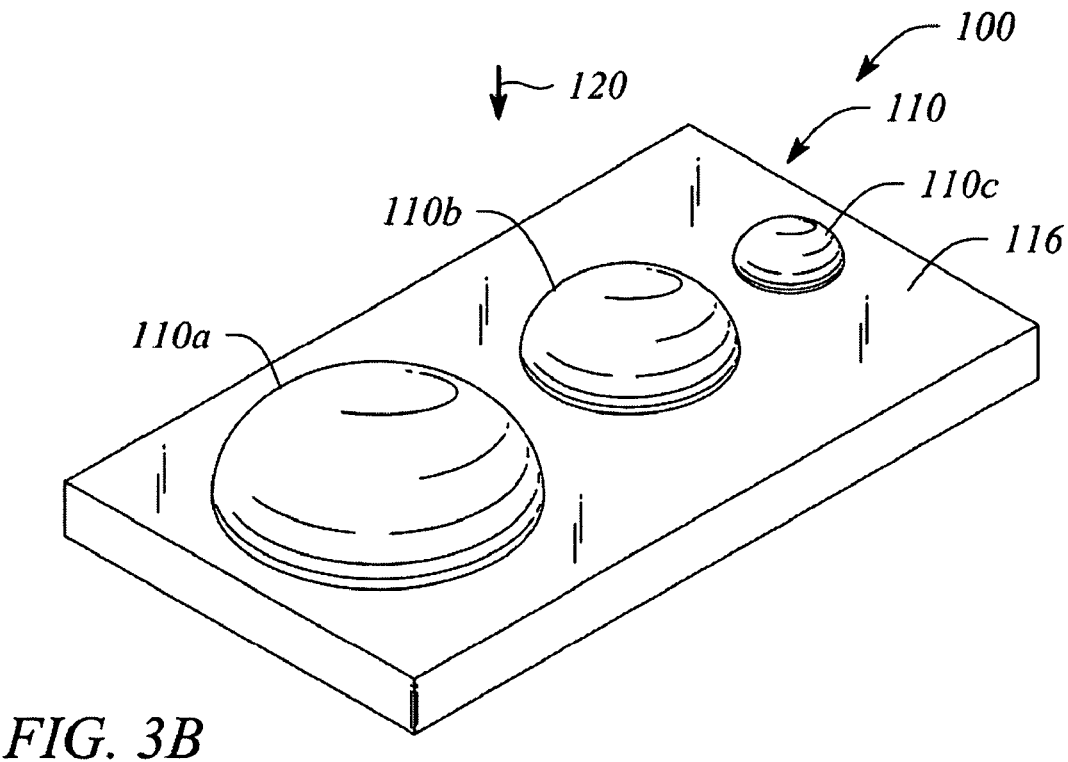

FIGS. 3A-3B illustrate a plasmonic conveyor 100, according to another embodiment of the present invention. In particular, FIG. 3A illustrates a top view a plasmonic conveyor 100 wherein a plurality of plasmonic elements 110 comprises adjacent but spaced apart spherical plasmonic elements 110a, 110b, as compared to the relative planar disks illustrated in FIG. 1A. For example, the spherical plasmonic elements 110a, 110b, may comprise spheres of a noble metal and range in size from about 10 nm to about 1 μm. FIG. 3B illustrates a perspective view of a plasmonic conveyor 100 comprising a plurality of plasmonic elements 110 that are domes or hemispherical in shape. For example, the dome-shaped plasmonic elements 110a, 110b may be formed in a surface of a substrate 116, as illustrated in FIG. 3B. FIG. 3B further illustrates a third plasmonic element 110c adjacent to the second plasmonic element 110b. In another example, the plasmonic elements may be spherical plasmonic elements, such as those illustrated in FIG. 3A, that are embedded in a surface of a substrate (not illustrated). In a perspective view, a partially embedded plurality of spherical plasmonic elements may have the same appearance as those illustrated in FIG. 3B, for example.

Figure 4:
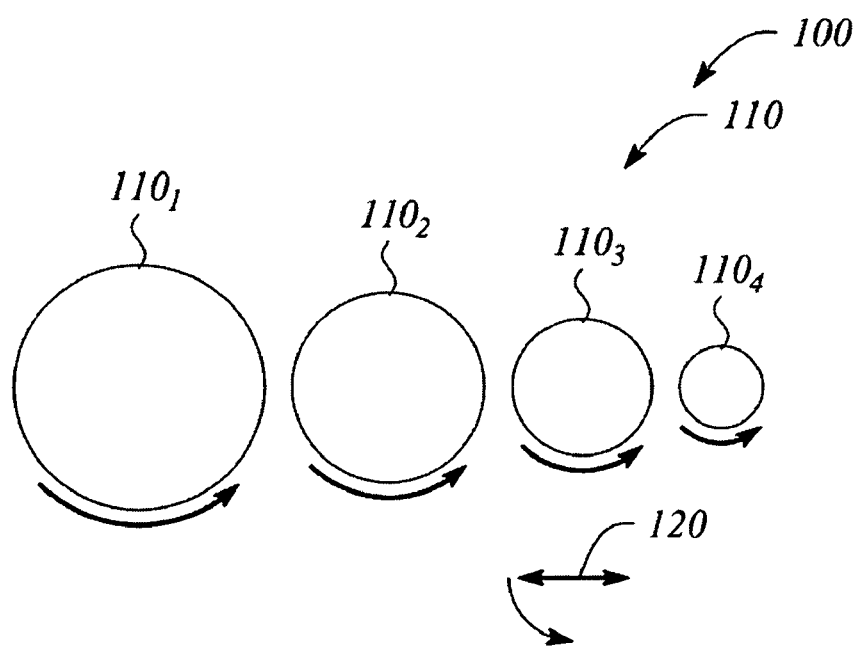
FIG. 4 illustrates a top view of a plasmonic conveyor, according to another embodiment of the present invention.

FIG. 4 illustrates a top view or a plasmonic conveyor 100, according to another embodiment of the present invention. The plasmonic conveyor 100 illustrated in FIG. 4 comprises a plurality of plasmonic elements 110 that form a cascade of n plasmonic elements $110_n$, ranging from large to small. A first plasmonic element $110_1$ is the largest member of the cascade while a second plasmonic element $100_2$ is smaller than the first, and so on. For example, the first plasmonic element $110_1$ may serve as an interface to an analyte particle source to attract and capture analyte particles (not illustrated). A last or n-th plasmonic element $110_n$, illustrated in FIG. 4 by way of example as a 4-th plasmonic element $110_4$ (i.e., n=4), may function as a final analyte holding point or a point of analysis (e.g., using SERS) within the cascade, for example. A series of curved arrows in FIG. 4 illustrates a trajectory of an analyte particle (not illustrated) along or 'down' the cascade of n plasmonic elements $110_n$ for a counterclockwise polarization rotation of an excitation signal 120. The transport of the analyte particle between adjacent plasmonic elements may be similar to the transport of analyte particles described above for FIGS. 2A-2E, for example.

Figure 5:
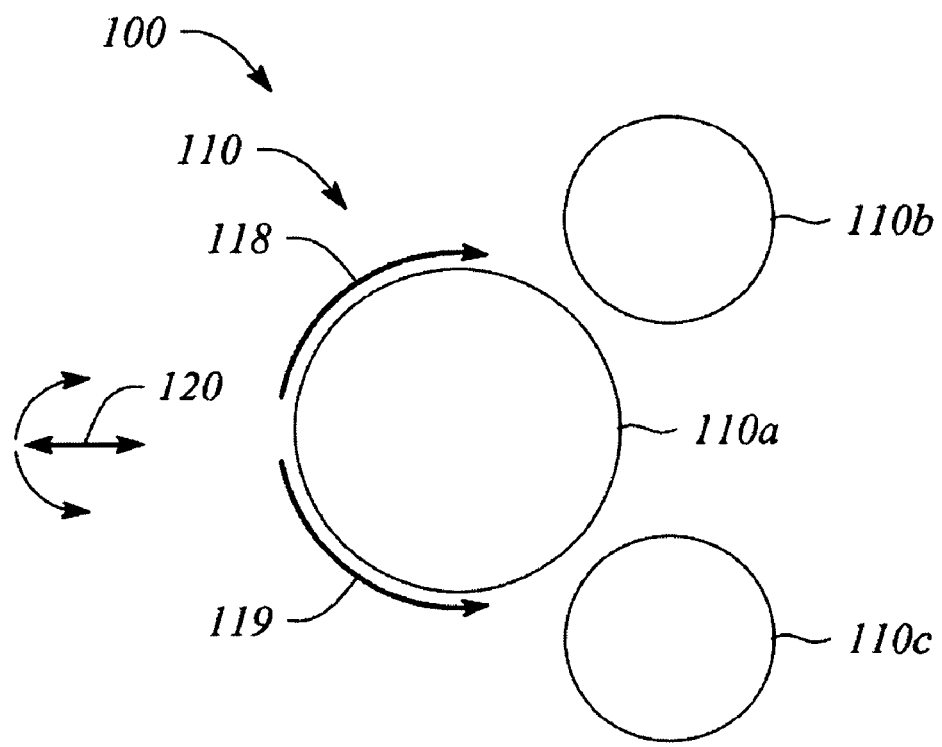
FIG. 5 illustrates a top view of a plasmonic conveyor, according to another embodiment of the present invention.

FIG. 5 illustrates a top view or a plasmonic conveyor 100, according to another embodiment of the present invention. The plasmonic conveyor 100 illustrated in FIG. 5 is configured as a transport switch comprising three plasmonic elements 110, by way of example. An analyte particle captured by a first plasmonic element 110a may be selectively transferred to either a second plasmonic element 110b or a third plasmonic element 110c by selectively controlling movement of a surface plasmon 112 on the surface of the first plasmonic element 110a.

For example, the first plasmonic element 110a may serve to capture an analyte particle from a source of analyte particles (not Illustrated) when a polarization of an excitation signal 120 is in a horizontal configuration. The captured analyte particle may be transported around the first plasmonic element 110a and subsequently transferred to the second plasmonic element 110b by rotating the polarization clockwise from the horizontal configuration. Alternatively, the captured analyte particle may be transported around the first plasmonic element 110a and subsequently transferred to the third plasmonic element 110c by rotating the polarization counterclockwise from the horizontal configuration, for example. Movement of the analyte particle in either the clockwise or the counterclockwise direction is indicated in FIG. 5 by respective curved arrows 118, 119.

As a result, an output (e.g., either the second or third plasmonic element 110b, 110c) may be determined by selecting which polarization rotation direction (e.g., clockwise or counterclockwise) is employed. The transport or hand-off from the first plasmonic element 110a to either the second plasmonic element 110b or the third plasmonic element 110c may be similar to the transport of the analyte particle 102 described above for FIGS. 2A-2E, for example. Moreover, a variable frequency may be used in lieu of or in addition to the polarization to implement the transport switch.

Figure 6:
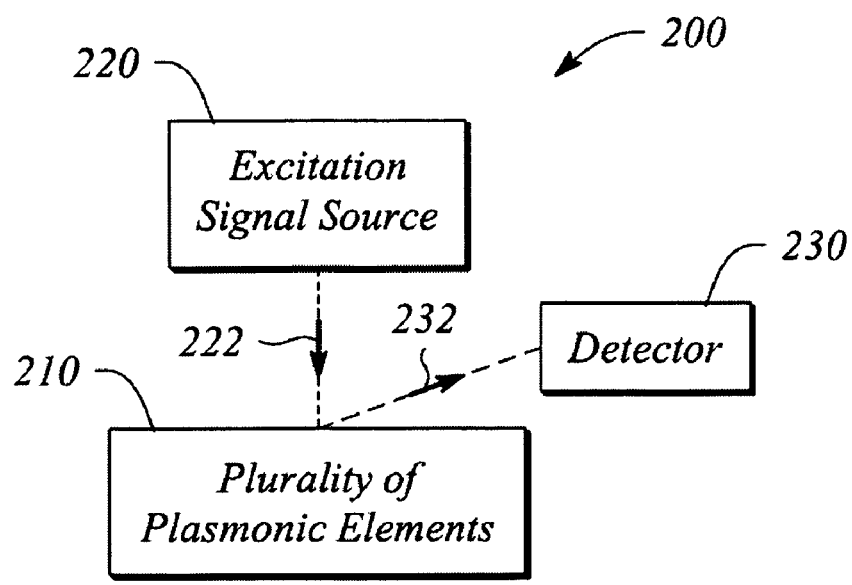
FIG. 6 illustrates a block diagram of a plasmonic conveyance system, according to an embodiment of the present invention.

FIG. 6 illustrates a block diagram of a plasmonic conveyance system 200, according to an embodiment of the present invention. The plasmonic conveyance system 200 comprises a plurality of plasmonic elements 210 that each individually supports a surface plasmon. A first plasmonic element of the plurality 210 is adjacent to a second plasmonic element of the plurality 210. In some embodiments, the plurality of plasmonic elements 210 is essentially similar to the plurality of plasmonic elements 110 described above with respect to the plasmonic conveyor 100.

The plasmonic conveyance system 200 further comprises an excitation signal source 220. The excitation signal source 220 provides an excitation signal 222 having a controllably variable one or both of polarization and frequency, for example. The excitation signal 222 excites a respective surface plasmon. Further, the controllably variable one or both of polarization and frequency controls and moves a location of the excited surface plasmon to transport an analyte particle. The analyte particle is carried by a high field region of the excited surface plasmon. In some embodiments, the excitation signal 222 provided by the excitation source 220 is essentially similar to the excitation signal 120 described above with respect to the plasmonic conveyor 100.

In some embodiments, the plasmonic conveyance system 200 further comprises a detector 230 that detects an emission spectrum produced by the analyte particle trapped in the high field region associated with the respective surface plasmon. For example, the detector 230 may comprise a Raman spectrum detector used to perform surface enhanced Raman spectroscopy (SERS) on the analyte particle. The detector 230 may detect a surface enhanced Raman spectrum signal 232 produced by the analyte particle, for example.

In some embodiments, the excitation signal 222 may comprise a controllable polarization that is periodically changed. For example, the polarization of the excitation signal may be periodically rotated from 0 degrees to 360 degrees. In some of these embodiments, the periodic change may produce a periodic variation in an intensity of the SERS signal 232 emitted by the analyte particle that facilitates detection of the SERS signal. For example, the periodic intensity variation of the SERS signal may enable filtering or time gating of an output of the detector 230 that improves a signal-to-noise ratio when detecting the SERS signal 232 emitted by the analyte particle. While SERS is described herein by way of example, similar results of periodically changing the polarization may be achieved with other field-intensity related spectrum detection approaches.

Figure 7:
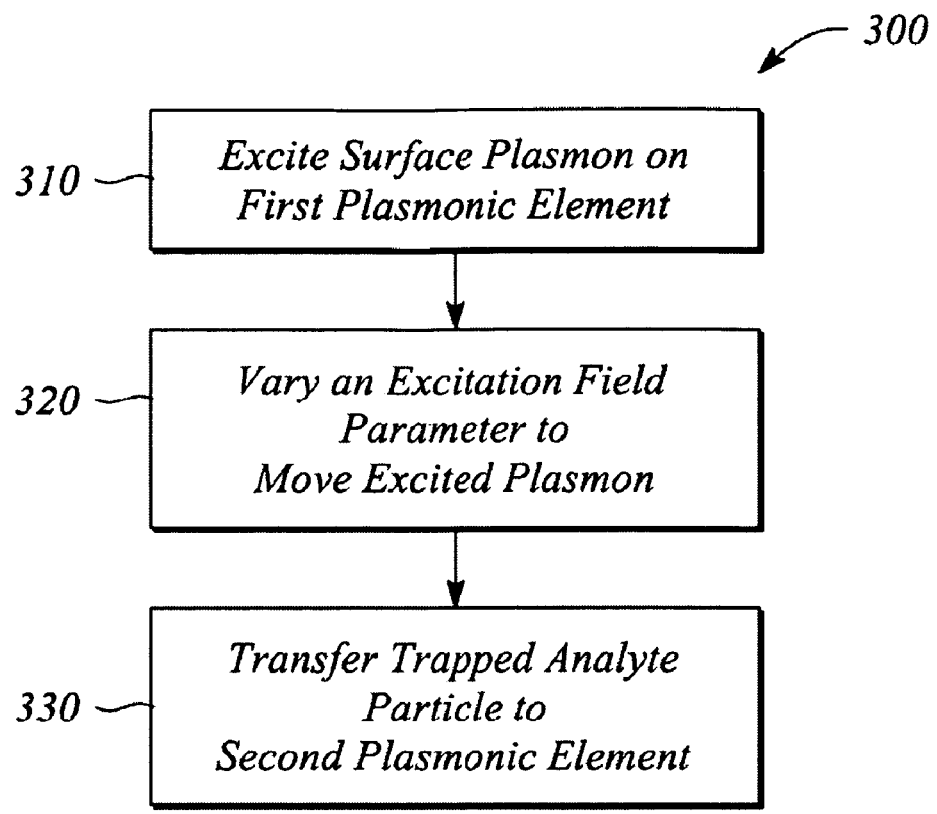
FIG. 7 illustrates a flow chart of a method of plasmonic conveyance, according to an embodiment of the present invention.

FIG. 7 illustrates a flow chart of a method 300 of plasmonic conveyance, according to an embodiment of the present invention. The method 300 of plasmonic conveyance comprises exciting 310 a surface plasmon on a first plasmonic element of a plurality of plasmonic elements. In some embodiments, exciting 310 a surface plasmon uses an excitation field having a polarization that is controllably variable. For example, the surface plasmon may be excited 310 using an excitation field having a linear polarization that may be rotated in a continuous manner through 360 degrees. Further, the exemplary polarization rotation may be selectively varied either in a clockwise or a counterclockwise direction. In another example, the excitation 310 may use an excitation field having a controllable variable frequency. The excitation field may be an electromagnetic field of an incident optical signal, for example.

The method 300 of plasmonic conveyance further comprises varying 320 a parameter of the excitation field including but not limited to, one or both of polarization and frequency, to move a location of the excited 310 surface plasmon. In some embodiments, an analyte particle trapped in and carried by a high field region associated with the surface plasmon is transported around a periphery of the surface of the first plasmonic element by the moved location of the surface plasmon. In some embodiment, the analyte particle is transported (i.e., translocated) as described above for the plasmonic conveyor 100.

In some embodiments (not illustrated), the method 300 of plasmonic conveyance Further comprises exciting a surface plasmon on a second plasmonic element of the plurality. The surface plasmon on the second plasmonic element may be excited by the same excitation field as is used to excite 310 the surface plasmon on the first plasmonic element, in some embodiments. In other embodiments, another excitation field may be employed.

In some of these embodiments, the method. 300 of plasmonic conveyance further comprises transferring 330 the trapped analyte particle to a high field region of a surface plasmon on the adjacent second plasmonic element. For example, the trapped analyte particle may be transferred 330 when the high field region of the surface plasmon on the adjacent second plasmonic element has a higher field intensity than that of the high field region associated with the surface plasmon on the first plasmonic element. Other ways for transferring 330 are discussed above with respect to the plasmonic conveyor 100. Regardless of how transferring 330 is accomplished, the trapped analyte particle is first transported from a location on the first plasmonic element to a vicinity of a high field region of the surface plasmon of another plasmonic element (e.g., a second plasmonic element) to facilitate transferring 330.

In some embodiments (not illustrated), the method 300 of plasmonic conveyance further comprises periodically varying the polarization of the excitation field. In such embodiments, the trapped analyte particle is periodically moved into and out of a combined high field region produced between the first plasmonic element and a second plasmonic element. Periodic exposure to the combined high field region may facilitate detection of an emission spectrum from the trapped analyte particle.

In particular, in some embodiments (not illustrated), the method 300 of plasmonic conveyance further comprises time gating a detector that receives an emission signal produced by the analyte particle. In some of these embodiments, the time gating is timed to coincide with a time period during which the analyte particle is in the combined high field region. The time gating may facilitate detection of the emission spectrum (e.g., a SERS signal) in the presence of noise.

Thus, there have been described embodiments of a plasmonic conveyor, plasmonic conveyor system, and a method of plasmonic conveyance that employ a surface plasmon that is controllably moved on a surface of a plasmonic element. It should be understood that the above-described embodiments are merely illustrative of some of the many specific embodiments that represent the principles of the present invention. Clearly, those skilled in the art can readily devise numerous other arrangements without departing from the scope of the present invention as defined by the following claims.

What is claimed is:

1. A plasmonic conveyor comprising:
   a first plasmonic element that supports a first surface plasmon;
   a second plasmonic element that supports a second surface plasmon, the second plasmonic element being adjacent to the first plasmonic element; and
   means for controlling a location of the first surface plasmon, the means for controlling providing controlled movement of the location on a surface of the first plasmonic element,
   wherein the controlled movement of the location of the first surface plasmon facilitates translocation of an analyte particle along a periphery of the first plasmonic element, the analyte particle being carried by a high field region of the first surface plasmon.

2. The plasmonic conveyor of claim 1, further comprising an excitation signal having one or both of a polarization and a frequency that is controllably variable, the excitation signal being incident on one or both of the first plasmonic element and the second plasmonic element to excite one or both of the first surface plasmon and the second surface plasmon, wherein the means for controlling a location comprises one or both of the controllably variable polarization and the controllably variable frequency of the excitation signal.

3. The plasmonic conveyor of claim 1, wherein the means for controlling facilitates translocation of the analyte particle to a vicinity of the second surface plasmon on a surface of the second plasmonic element, the means for controlling further facilitating transfer of the analyte particle from the high field region of the first surface plasmon to a high field region of the second surface plasmon.

4. The plasmonic conveyor of claim 3, wherein the second surface plasmon high field region has a higher field strength than a field strength of the first surface plasmon high field region such that the transported analyte particle is preferentially retained by the second surface plasmon high field region when the location of the first surface plasmon is moved away from the vicinity of the second plasmon.

5. The plasmonic conveyor of claim 1, wherein the second plasmonic element is smaller than the first plasmonic element, the means for controlling further controlling a location of the second surface plasmon on a surface of the second plasmonic element.

6. The plasmonic conveyor of claim 1, wherein one or both of the first plasmonic element and the second plasmonic element comprise a disk having one of a circular circumference and an elliptical circumference, the respective surface plasmon being excited on a surface of a circumferential edge of the disk.

7. The plasmonic conveyor of claim 1, further comprising a third plasmonic element that supports a third surface plasmon, the means for controlling a location facilitating both selectable translocation and subsequent transfer of the analyte particle to a high field region of one of the second surface plasmon and the third surface plasmon, wherein the plasmonic conveyor is a selectable transfer switch for the transported analyte particle.

8. The plasmonic conveyor of claim 1, further comprising a Raman spectrum detector that detects a surface enhanced Raman spectrum signal produced by the analyte particle.

9. A plasmonic conveyance system comprising:
a plurality of plasmonic elements that each individually supports a surface plasmon, a first plasmonic element of the plurality being adjacent to a second plasmonic element of the plurality; and
an excitation signal source that provides an excitation signal having a controllably variable one or both of polarization and frequency, the excitation signal exciting a respective surface plasmon,
wherein the controllably variable one or both of polarization and frequency controls and moves a location of the excited surface plasmon to transport an analyte particle, the analyte particle being carried by a high field region of the excited surface plasmon.

10. The plasmonic conveyor system of claim 9, further comprising a detector that detects a surface enhanced Raman spectrum (SERS) signal produced by the analyte particle, the controllably variable one or both of polarization and frequency of the excitation signal being periodically changeable, wherein a periodic change to the polarization produces a periodic variation in an intensity of the SERS signal, the periodic variation in intensity facilitating detection of the SERS signal.

11. A method of plasmonic conveyance, the method comprising:
exciting a surface plasmon on a first plasmonic element of a plurality of plasmonic elements using an excitation field having one or both of a polarization and a frequency that is controllably variable;
varying one or both of the polarization and the frequency of the excitation field to move a location of the excited surface plasmon, the surface plasmon being moved on a surface of the first plasmonic element,
wherein an analyte particle trapped in a high field region of the excited surface plasmon is transported around a periphery of the first plasmonic element by the moved location of the excited surface plasmon.

12. The method of plasmonic conveyance of claim 11, further comprising:
exciting a surface plasmon on an adjacent second plasmonic element of the plurality; and
transferring the trapped analyte particle to a high field region of the excited surface plasmon on the adjacent second plasmonic element,
wherein transferring comprises one or both of moving the locations of the respective excited surface plasmons of the first plasmonic element and the second plasmonic element until the respective high field regions overlap and switching off the surface plasmon on the first plasmonic element while switching on the surface plasmon on the second plasmonic element.

13. The method of plasmonic conveyance of claim 12, wherein the high field region of the surface plasmon of the second plasmonic element has a higher field intensity than a field intensity of the surface plasmon of the first plasmonic element, the transferred analyte particle being preferentially retained by the higher field region of the surface plasmon of the second plasmonic element.

14. The method of plasmonic conveyance of claim 11, further comprising periodically varying one or both of the polarization and the frequency of the excitation field such that the trapped analyte particle is periodically moved into and out of a combined high field region produced between the first plasmonic element and a second plasmonic element.

15. The method of plasmonic conveyance of claim 14, further comprising time gating a detector that receives an emission signal produced by the analyte particle, the time gating coinciding with a time period during which the analyte particle is in the combined high field region.

* * * * *